(12) United States Patent
Schmidt et al.

(10) Patent No.: US 6,248,571 B1
(45) Date of Patent: *Jun. 19, 2001

(54) METHOD OF PRODUCING DIHYDROXYPYRIMIDINE DERIVATIVES

(75) Inventors: Beat Schmidt, Baltschieder; Andreas Kiener, Visp; John McGarrity, Glis, all of (CH)

(73) Assignee: Lonza AG, Gampel/Valais (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 31 days.

(21) Appl. No.: 09/029,230

(22) PCT Filed: Aug. 30, 1996

(86) PCT No.: PCT/EP96/03826

§ 371 Date: Feb. 25, 1998

§ 102(e) Date: Feb. 25, 1998

(87) PCT Pub. No.: WO97/08152

PCT Pub. Date: Mar. 6, 1997

(30) Foreign Application Priority Data

Aug. 31, 1995 (CH) .................................................. 2474/95

(51) Int. Cl.⁷ ...................................................... C12P 17/12
(52) U.S. Cl. .......................... 435/122; 435/129; 435/227; 435/191; 435/252.1; 435/135; 435/136; 534/767; 558/303
(58) Field of Search .................................. 435/122, 129, 435/227, 191, 252.1, 170, 135, 136; 534/767; 558/303

(56) References Cited

FOREIGN PATENT DOCUMENTS

1092144 * 1/1968 (GB) .
6256278 * 9/1994 (JP) .

OTHER PUBLICATIONS

Yokoyama et a. "Asymmetric hydrolysis of a disubstituted malononitrile by the aid of a microorganism," Tetrahedron Asymm. (1993) 4(6): 1081–84.*

Ingvorsen et al. "Microbial hydrolysis of organic nitriles and amides," CIBA Foundation Symposium (1988) 140:16–31.*

* cited by examiner

Primary Examiner—Irene Marx
(74) Attorney, Agent, or Firm—Fisher, Christen & Sabol

(57) ABSTRACT

A process for the preparation of dihydroxypyrimidine derivatives of the general formula:

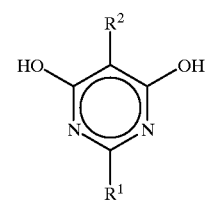

I in which $R^1$ and $R^2$ are identical or different and are a hydrogen atom, aryl group, or a $C_1$–$C_4$-alkyl group or an aryl group, starting from a compound of the general formula:

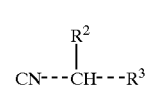

II in which $R^2$ has the meaning mentioned above and $R^3$ is —CN or $COOR^4$, in which $R^4$ is a $C_1$–$C_4$-alkyl group.

16 Claims, No Drawings

METHOD OF PRODUCING DIHYDROXYPYRIMIDINE DERIVATIVES

This application was filed under 35 USC 371 as the national phase of PCT/EP96/03826 filed Aug. 30, 1996.

BACKGROUND OF THE INVENTION

1. Field of the Invention

The invention relates to a novel process for the preparation of dihydroxypyrimidine derivatives of the general formula

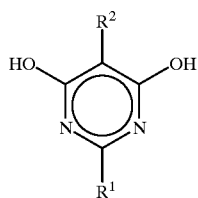

I in which $R^1$ and $R^2$ are identical or different and are a hydrogen atom, aryl group or a $C_1$–$C_4$-alkyl group, starting from a compound of the general formula

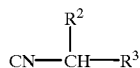

II in which $R^2$ has the meaning mentioned and $R^3$ is —CN or $COOR^4$, in which $R^4$ is a $C_4$–$C_4$-alkyl group.

2. Background Art

Dihydroxypyrimidine is an important intermediate for the preparation of insecticides such as, for example, for the preparation of 4,6-pyrimidinediyl-bis(thiono)(thiol)phosphoric(phosphonic) acid esters (DE 25 23 324).

To date, several processes for the preparation of dihydroxypyrimidine or its derivatives are known.

For example, the preparation of dihydropyrimidine starting from malonamide (German Patent Specification 12 00 308) is known. In this preparation, malonamide is cyclized with formamide in the presence of sodium methanolate to give the dihydroxypyrimidine.

This process has the disadvantage that the starting material malonamide is relatively costly.

D. J. Brown (J. Chem. Soc., 1956, pp. 2312–2314) also describes a process for the preparation of dihydroxypyrimidine starting from malonamide. In this process, malonamide is cyclized in the presence of sodium ethoxide and ethyl formate to give the dihydroxypyrimidine. This process on the one hand has the disadvantage that dihydroxypyrimidine is only obtained in moderate yield. On the other hand, as already described above, the starting material malonamide is relatively costly.

JP 4260 comprises a process for the preparation of dihydroxypyrimidine by reaction of malonate with formamide in the presence of an alkali metal alkoxide. A disadvantage of this process is that the formamide has to be used in a large excess.

U.S. Pat. No. 17 66 748 describes a process for the preparation of 2-aryl-4,6-dihydroxy-pyrimidines starting from diethyl malonate. In this process, diethyl malonate is cyclized in the presence of an amidine of an arylcarboxylic acid to give the corresponding product. This process has the disadvantage that the corresponding amidines are very costly.

The object of the present invention was to make available a more economical and ecologically more favourable process for the preparation of dihydroxypyrimidine derivatives, in which the dihydroxypyrimidine can be isolated in good yield and purity.

This object was achieved by the novel process according to the invention.

In the first process stage, as substrate, a compound of the general formula

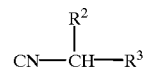

II in which $R^2$ and $R^3$ have the meaning mentioned, is converted by means of microorganisms of the genus Rhodococcus into a malonic acid derivative of the general formula

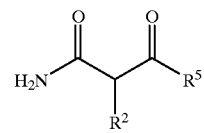

III in which $R^2$ has the meaning mentioned and $R^5$ is a $C_1$–$C_4$-alkoxy group or $NH_2$.

The compounds of the general formula II such as methyl or ethyl cyanoacetate are commercially available compounds.

Expediently, the first stage is carried out using microorganisms of the species Rhodococcus rhodochrous, Rhodococcus sp. 5–6 or Rhodococcus equi, preferably using microorganisms of the species Rhodococcus sp. 5–6 (FERM BP-687), Rhodococcus rhodochrous J1 (FERM BP-1478) or using microorganisms of the species Rhodococcus equi TG328 (FERM BP-3791 or DSM 6710). In particular, the reaction is carried out by means of microorganisms of the species Rhodococcus rhodochrous (FERM BP-1478). The microorganisms of the species Rhodococcus sp. 5–6, Rhodococcus rhodochrous J1 and Rhodococcus equi TG328 are microorganisms described in the literature. Rhodococcus rhodochrous J1 (FERM BP-1478) is described in detail in EP-B 307 928, Rhodococcus sp. 5–6 (FERM BP-687) in EP-A 0 188 316 and Rhodococcus equi TG328 (FERM BP-3791) in U.S. Pat. No. 5,258,305.

As is described in U.S. Pat. No. 5,334,519, Strain J-1 of species Rhodococcus rhodochrous was sampled from the soil in Sakyo-ku of Kyoto, Japan, and deposited as an international deposit (under the Budapest Treaty on the International Recognition of the Deposit of Microorganisms for the Purposes of Patent Procedure) in the Fermentation Research Institute, Japan, Agency of Industrial Sciences and Technology with the accession number of Bikoken-joki No. 1478 (FERM BP-1478). According to the subject Receipt in the Case of an Original Deposit, this deposit occurred on Sep. 18, 1987.

Also suitable for the process are the functionally equivalent variants and mutants of these microorganisms. "Functionally equivalent variants and mutants" are understood as meaning microorganisms which essentially have the same properties and functions as the original microorganisms. Variants and mutants of this type can be randomly formed, for example, by means of UV irradiation.

Customarily, the microorganisms are cultured (grown) according to EP-B 307 928 before the actual biotransformation and the active enzymes are induced. Preferably, the biotransformation is carried out, in a manner customary to those skilled in the art, using immobilized microorganism cells.

Expediently, the biotransformation is carried out in a pH range from 3 to 7, preferably in a pH range from 4 to 6.

The biotransformation can be carried out at a temperature from 0 to 30° C., preferably from 3 to 20° C.

As substrates, compounds of the general formula II are used in which $R^2$ is a hydrogen atom, aryl group or a $C_1$–$C_4$-alkyl group and $R^3$ is —CN or COOR$^4$, in which $R^4$ is a $C_1$–$C_4$-alkyl group. As a $C_1$–$C_4$-alkyl group, methyl-, ethyl-, propyl-, i-propyl-, butyl-, i-butyl- or t-butyl- can be used. As aryl-, for example, phenyl-, substituted or unsubstituted, or naphthyl- can be used. Preferably, $R^2$ is a hydrogen atom and $R^3$ is methyl-, ethyl-, i-propyl- or —CN.

After a customary reaction time of 1 to 100 h, the amides formed can be isolated in a simple manner, e.g. by removal of water.

In the second process stage, the malonic acid derivative of the general formula

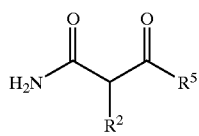

III is cyclized with a carboxamide of the general formula

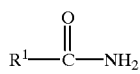

IV in the presence of a base to give the final product according to formula I.

The radical $R^5$ is a $C_1$–$C_4$-alkoxy group such as methoxy-, ethoxy-, propoxy-, butoxy-, i-butoxy-, t-butoxy- or —NH$_2$. Preferably, $R^5$ is methoxy- or ethoxy-. The radical $R^2$ has the definition already described.

The radical $R^1$ is either $C_1$–$C_4$-alkyl- such as methyl-, ethyl-, propyl-, i-propyl-, butyl-, t-butyl-, i-butyl- or a hydrogen atom. Preferably, $R^1$ is a hydrogen atom.

Expediently, the carboxamide is used in a ratio from 2 to 8 mol per mole of malonic acid derivative, preferably in a ratio of 2 to 3 mol.

As a base, expediently an alkali metal alcoholate such as sodium or potassium methanolate, ethanolate, propanolate, butanolate, i-butanolate, t-butanolate, amylate or i-amylate is used. Preferably, sodium methanolate is used.

The concentration of the base can vary in a range from 2 to 6 mol per mole of malonic acid derivative, preferably in a range from 3 to 4 mol.

As solvents for the second stage, polar solvents such as methanol, ethanol, propanol or butanol can be used, preferably methanol is used.

Expediently, the second stage is carried out at a temperature from 30° C. up to the reflux temperature of the corresponding solvent, preferably at reflux temperature of the corresponding solvent.

After a further reaction time of 1 to 6 h, the dihydroxypyrimidine derivative of the formula I can be isolated by customary working-up methods.

DETAILED DESCRIPTION OF THE INVENTION

EXAMPLE 1

Preparation of Malonic Acid Monoamide Monoesters (Carbamoylacetic Acid Esters) from Methyl Cyanoacetate, Ethyl Cyanoacetate and Isopropyl Cyanoacetate In a glass vessel equipped with a magnetic stirrer, 200 ml of water, 0.62 g of J1 biomass (FERM BP-1478) (calculated as dry weight) and 50 g of the corresponding cyanoacetic acid ester were incubated at room temperature for 16 hours. The pH was approximately 5. By means of GC analysis, starting material could no longer be detected at this time. The biomass was filtered off and the water was removed from the product under reduced pressure. Traces of water were then removed azeotropically by addition of toluene to the residue. The isolated yield was >90% and the purity of the carbamoylacetic acid ester formed was >95% according to GC. Isopropyl carbamoylacetate precipitated from aqueous solution under these conditions during the biotransformation. In this case, the suspension was first warmed to 50° C. in order to bring the isopropyl ester into solution before filtering off the biomass.

EXAMPLE 2

Influence of the pH on the Conversion of Methyl Cyanoacetate to Methyl Carbamoylacetate A 1 l Applikon fermenter was used for the experiments. The biotransformation batch contained 200 g of methyl cyanoacetate, 800 ml of water and 1.2 g of J1 biomass (FERM BP-687) (calculated as dry weight). The vessel was stirred at 200 rpm and the temperature was 12° C.–17° C. The reaction was terminated after 16 h. It was not possible to detect any starting material at this time by means of GC analysis. The pH in batch A was not kept constant and fell from an initial value of 5.7 to 4.7 at the end of the reaction.

In batch B the pH during the entire reaction time was kept constant at a value of 8.0. To do this, 30% NaOH solution was used.

Working up was carried out as described above.

By means of titration, it was possible to detect a significant amount of methyl carbamoylacetate both in batch A and in batch B. In contrast to batch B, however, the product in batch A was significantly purer.

EXAMPLE 3

Conversion of Malononitrile to Malonamide Using J1 Biomass (FERM BP-1478)

In a glass vessel equipped with a magnetic stirrer, 90 ml of water, 0.3 g of J1 biomass (calculated as dry weight) and 10 g of malononitrile were incubated at room temperature for 6 h. It was no longer possible to detect any starting material at this time by means of GC analysis. Malonamide precipitated from aqueous solution under these conditions during the biotransformation. The suspension was warmed to 50° C. in order to bring the product into solution before the biomass was filtered off.

The water was removed from the product under reduced pressure. The isolated yield was >90% and the purity of the malonamide formed was >95% (GC).

EXAMPLE 4

Preparation of Dihydroxypyrimidine ($R^1$=$R^2$=H)

Formamide (26.43 g; 575 mmol) was added to sodium methylate solution (157.56 g; 875 mmol) at room temperature in the course of 5 minutes, the solution warming to 28° C. The solution was heated to reflux (64° C.) and kept at this temperature for 15 minutes. Malonic acid monoamide monoester, dissolved in 30 ml of methanol, was added dropwise to this warm solution at 64° C. In the course of this a colourless suspension gradually resulted. The readily stirrable suspension was refluxed for 3 h and then cooled to room temperature. 125 ml of water were added such that the temperature was about 25° C. At the end of the addition, a slightly yellow solution was obtained. The pH was adjusted to 4.0 by the addition of 82.0 g of conc. HCl solution (the temperature was between 25 and 30° C.). The suspension was stirred at room temperature for 15 min, and the precipitated solid was filtered off and thoroughly washed twice with 45 ml of water. The pale yellow solid was dried in a vacuum drying oven at 60° C. for 24 h. 22.67 g (content 97.0% according to HPLC), corresponding to a yield of 78.5%, were obtained.

$^1$H NMR (DMSOd$_{d6}$) δ: 5.22 (s, 1H); 8.05 (s, 1H); 11.5–12.2 (s, br, 2H).

$^{13}$C NMR (DMSOd$_{d6}$) δ: 89.99; 149.90; 166.17.

What is claimed is:

1. A process for the preparation of a dihydroxypyrimidine compound of formula:

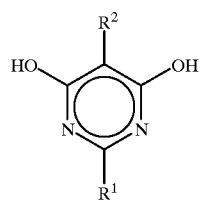

I in which $R^1$ and $R^2$ are identical or different and are a hydrogen atom, a $C_1$–$C_4$-alkyl group or an aryl group, comprising in a first stage, converting, as a substrate, a compound of formula:

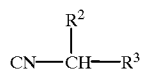

II in which $R^2$ has the meaning mentioned above and $R^3$ is —CN or COOR$^4$, in which $R^4$ is a $C_1$–$C_4$-alkyl group, using microorganisms of the strain *Rhodococcus rhodochrous* J1 or mutants thereof which produce malonic acid derivatives of formula III, into a malonic acid compound of formula:

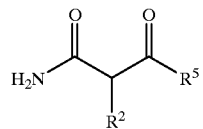

III in which $R^2$ has the meaning mentioned above and $R^5$ is a $C_1$–$C_4$-alkoxy group or —NH$_2$, and, in a second stage, cyclizing said malonic acid compound III with a carboxamide of formula:

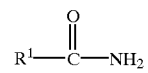

IV in which $R^1$ has the meaning mentioned above in the presence of a base to give the dihydroxypyrimidine compound of formula I.

2. The process according to claim 1, wherein the conversion is carried out in the first stage using immobilized microorganisms of the strain *Rhodococcus rhodochrous* J1 or mutants thereof which produce malonic acid derivatives of formula III.

3. The process according to claim 2, wherein the conversion in the first stage is carried out at a pH from 3 to 7 and a temperature from 0° to 30° C.

4. The process according to claim 3, wherein in the first stage methyl cyanoacetate, ethyl cyanoacetate, isopropyl cyanoacetate, or malononitrile is used as the compound of formula II.

5. The process according to claim 4, wherein in the second stage malonic acid monoamide monomethyl ester or malonic acid monoamide monoethyl ester is used as the malonic acid compound.

6. The process according to claim 5, wherein in the second stage formamide is used as the carboxamide.

7. The process according to claim 6, wherein in the second stage an alkali metal alcoholate is used as the base.

8. The process according to claim 7, wherein the second stage is carried out at a temperature from 30° C. up to the reflux temperature of the corresponding solvent.

9. The process according to claim 1, wherein the conversion in the first stage is carried out at a pH from 3 to 7 and a temperature from 0° to 30° C.

10. The process according to claim 1, wherein in the first stage methyl cyanoacetate, ethyl cyanoacetate, isopropyl cyanoacetate or malononitrile is used as the compound of formula II.

11. The process according to claim 1, wherein in the second stage malonic acid monoamide monomethyl ester or malonic acid monoamide monoethyl ester is used as the malonic acid compound.

12. The process according to claim 1, wherein in the second stage formamide is used as the carboxamide.

13. The process according to claim 1, wherein in the second stage an alkali metal alcoholate is used as the base.

14. The process according to claim 1, wherein the second stage is carried out at a temperature from 30° C. up to the reflux temperature of the corresponding solvent.

15. A process for the preparation of a malonic acid compound of formula:

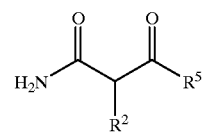

III in which $R^2$ and $R^5$ are identical or different and are a hydrogen atom, a $C_1$–$C_4$-alkyl group or an aryl group, comprising converting a compound of formula:

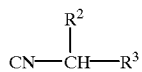

II in which R² has the meaning mentioned above and R³ is —CN or COOR⁴, in which R⁴ is a $C_1$–$C_4$-alkyl group, provided that when R² is hydrogen, R³ is not —CN, into the malonic acid of formula III, using microorganisms of the strain *Rhodococcus rhodochrous* J1 or mutants thereof which produce malonic acid derivatives of formula III.

16. The process according to claim 15, wherein the conversion is carried out at a temperature from 0° C. and at a pH from 3 to 7.

* * * * *